US011008516B2

(12) United States Patent
Lan

(10) Patent No.: US 11,008,516 B2
(45) Date of Patent: May 18, 2021

(54) LIQUID CRYSTAL MATERIAL AND LIQUID CRYSTAL DISPLAY PANEL

(71) Applicant: Shenzhen China Star Optoelectronics Semiconductor Display Technology Co., Ltd., Guangdong (CN)

(72) Inventor: Song Lan, Guangdong (CN)

(73) Assignee: SHENZHEN CHINA STAR OPTOELECTRONICS SEMICONDUCTOR DISPLAY TECHNOLOGY CO., LTD., Guangdong (CN)

(*) Notice: Subject to any disclaimer, the term of this patent is extended or adjusted under 35 U.S.C. 154(b) by 323 days.

(21) Appl. No.: 15/781,591

(22) PCT Filed: Mar. 19, 2018

(86) PCT No.: PCT/CN2018/079423
§ 371 (c)(1),
(2) Date: Jun. 5, 2018

(87) PCT Pub. No.: WO2019/165653
PCT Pub. Date: Sep. 6, 2019

(65) Prior Publication Data
US 2020/0270526 A1    Aug. 27, 2020

(30) Foreign Application Priority Data
Mar. 1, 2018  (CN) .................. 201810170112.X

(51) Int. Cl.
*C09K 19/56*    (2006.01)
*C07D 233/32*   (2006.01)
(Continued)

(52) U.S. Cl.
CPC ............ *C09K 19/56* (2013.01); *C07D 233/32* (2013.01); *G02F 1/1337* (2013.01);
(Continued)

(58) Field of Classification Search
CPC ............ C09K 19/56; C09K 2019/0425; G02F 1/1337; G02F 1/133703
See application file for complete search history.

(56) References Cited

U.S. PATENT DOCUMENTS

2013/0314655 A1   11/2013  Archetti et al.
2017/0210994 A1*   7/2017  Lim .................. G02F 1/134309
(Continued)

FOREIGN PATENT DOCUMENTS

CN    103492531 A    1/2014
CN    104845644 A    8/2015
(Continued)

*Primary Examiner* — Chanceity N Robinson
*Assistant Examiner* — Anna Malloy

(57) ABSTRACT

A liquid crystal material and a liquid crystal display panel includes a liquid crystal material including liquid crystal molecules, a polymerizable monomer, and an auxiliary alignment agent. A structural formula of the auxiliary alignment agent is:

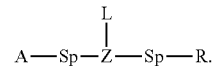

The A group includes at least one oxygen atom, at least one nitrogen atom, or at least one oxygen atom and at least one nitrogen atom, the Sp group essentially is a —$(CH_2)_n$— group, the Z group is selected from:

(Continued)

-continued

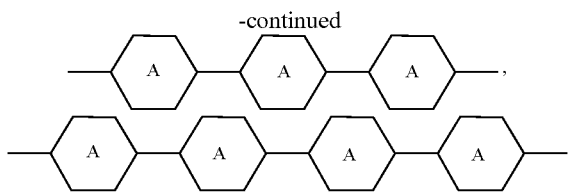

and any combination thereof, the R group is a straight or branched first alkyl group containing 5 to 20 carbon atoms, and the L group is selected from:

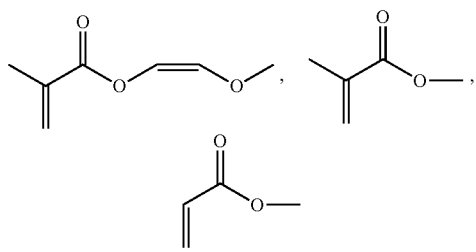

and any combination thereof.

5 Claims, 1 Drawing Sheet

(51) Int. Cl.
*G02F 1/1335* (2006.01)
*G02F 1/1337* (2006.01)
*C09K 19/04* (2006.01)

(52) U.S. Cl.
CPC ............... *G02F 1/133514* (2013.01); *C09K 2019/0425* (2013.01); *C09K 2019/0448* (2013.01); *G02F 1/133742* (2021.01)

(56) References Cited

U.S. PATENT DOCUMENTS

| | | |
|---|---|---|
| 2017/0322459 A1 | 11/2017 | Zhong |
| 2018/0023001 A1* | 1/2018 | Tanaka .............. C09K 19/3001 252/299.4 |
| 2018/0057743 A1* | 3/2018 | Archetti ............ C09K 19/3852 |
| 2018/0171231 A1 | 6/2018 | Archetti et al. |
| 2018/0208848 A1 | 7/2018 | Archetti et al. |

FOREIGN PATENT DOCUMENTS

| | | |
|---|---|---|
| CN | 105001879 A | 10/2015 |
| CN | 106536679 A | 3/2017 |
| WO | 2017041893 A1 | 3/2017 |

* cited by examiner

| a substance a (0.02 mol) and a substance b (0.02 mol) of are dissolved in toluene (200 mL), and 100 mL of ethanol and 40 mL of $Na_2CO_3$ solution with a concentration of 1 mol/L are added into the toluene, a rare gas, such as argon, is introduced into the toluene, after 30 minutes, Tetrakis-(triphenylphosphine) palladium (100 mg) was added into the toluene so as to form a mixed solution, the mixed solution is heated to reflux for 60 min, finally, after separation, a substance c is obtained. | S10 |

↓

| the compound c (0.01 mol) is dissolved in 50 mL of a dichloromethane solution and cool to -28°C, then, 0.02 mol of boron trifluoride was added to the cooled mixed dichloromethane solution, and the cooled mixed dichloromethane solution is stirred at -25°C for 3 hours while reacting, finally, under a condition of an ice bath, a NaOH solution (having a substance concentration of 2 mol/L) is added to the mixed dichloromethane solution, and a substance d is obtained after separation and purification | S20 |

↓

| the compound d ($4\times10^{-3}$ mol), methacrylic acid ($6\times10^{-3}$ mol) and 4-(dimethylamino)pyridine ($2\times10^{-4}$ mol) are dissolved in a dichloromethane solution (25 mL) for forming a mixed dichloromethane solution, and the mixed dichloromethane solution is cooled to 1°C, secondly, the cooled mixed dichloromethane solution is gradually added dropwise a dichloromethane solution containing carbodiimide ($6\times10^{-3}$ mol) so as to from a dropping process system, a temperature of the dropping process system is maintained at 1~4°C, finally, a reaction of the dropping process system is stirred at a room temperature for 18 hours, and a compound e is obtained after separation and purification | S30 |

LIQUID CRYSTAL MATERIAL AND LIQUID CRYSTAL DISPLAY PANEL

FIELD OF INVENTION

This disclosure relates to display panel manufacturing technology, and more particularly to a liquid crystal material and liquid crystal display panel.

BACKGROUND OF INVENTION

With development of display technology, liquid crystal displays (LCDs) and other display panel devices have advantages, such as high image quality, power saving, thin body, and widely used, for wide applications in mobile phones, televisions, personal digital assistants, digital cameras, notebook computers, desktop computers, and other consumer electronics products, and have become mainstream in display devices.

Most liquid crystal display devices on the current market are backlit liquid crystal displays, which comprise liquid crystal display panels and backlight modules (BM). A working principle of the liquid crystal display panel is to dispose liquid crystal molecules between two parallel glass substrates. There are many vertical and horizontal small wires between the two parallel glass substrates. The liquid crystal molecules are controlled to change direction by energizing or not energizing for refracting light of the backlight module to generate a picture.

Thin film material layers are disposed on a CF substrate and a TFT substrate of a liquid crystal display, respectively. Its main function is to align the liquid crystal molecules in a certain direction. We call it an alignment film (usually polyimide (PI) material). The alignment film mainly includes a frictional alignment PI material and a photo-alignment PI material. However, each kind of alignment material has its own disadvantages. First of all, friction alignment can easily cause dust particles, static electricity residue, brush marks and other problems, thereby reducing process yield. Photo-alignment materials can avoid these problems. However, due to limited material properties, poor heat resistance and aging resistance, and an ability to anchor LC molecules simultaneously is weak, and quality of a panel is affected. Secondly, PI material itself has high polarity and high water absorption, storage and transportation of the PI material are prone to spoilage resulting in uneven alignment, and the PI material is expensive. A process of film formation of the PI material on TFT-LCD is also more complicated, resulting in increased panel costs.

Therefore, there are some small-molecule additive materials that can replace the PI materials. It mainly includes alkyl chain-containing silanes, cage-type silsesquioxanes, alkyl chain-containing alcohols, and the like. These small-molecule additive materials mainly rely on their own polar groups to adsorb on a surface of a substrate, so that the liquid crystal molecules can be vertically oriented. A liquid crystal material containing the additive material is called a self-aligned liquid crystal material.

Applying this material to TFT-LCD panels often has problems, such as LCD panel topography surface difference. A main reason is that a surface structure of the TFT-LCD panel is a "*" slit pattern. An area where a pixel electrode is located is divided into an area covered by an ITO pixel electrode and an area not covered by the ITO pixel electrode, while the area not covered by ITO pixel electrode is mainly a passivation layer. The passivation layer is generally comprises a inorganic material silicon nitride and an organic material insulating film PFA (Polymer Film on Array). When a PI alignment layer is not applied, and the additive material is adsorbed on the surface of the substrate for alignment, due to the weak interaction between the additive material and the SiNx/PFA, a difference in an acting force between an auxiliary alignment agent and the surface of the substrate leads to poor alignment. It is easy to cause drawbacks, such as dark lines or bright lines, after a voltage is applied.

Thus, it is necessary to improve the additive material so as to improve a function of anchoring the substrate, and solve the problems of alignment force difference, the drawbacks of the bright lines and the dark lines due to pixel electrode differences, thereby achieving uniform alignment.

SUMMARY OF INVENTION

The disclosure provides a liquid crystal material and liquid crystal display panel for solving the problems of alignment force difference, the drawbacks of the bright lines and the dark lines due to differences of the conventional pixel electrode.

In order to solve the above-mentioned drawbacks, the disclosure provides a technical solution as follow.

The disclosure provides a liquid crystal material. The liquid crystal material comprises liquid crystal molecules, a polymerizable monomer, and an auxiliary alignment agent.

A structural formula of the auxiliary alignment agent comprises at least one A group, at least one Sp group, at least one Z group, at least one R group, and at least one L group.

The A group comprises at least one oxygen atom, at least one nitrogen atom, or at least one oxygen atom and at least one nitrogen atom.

The Sp group is a —(CH$_2$)$_n$— group, or a substituted group thereof obtained by substituting one or more —CH$_2$ groups in the —(CH$_2$)$_n$— group with one or more groups selected from —O—, —S—, —CO—, —CO—O—, —O—CO—, —O—CO—O—, —OCH$_2$—, —CH$_2$O—, —CH=CH—, —CF=CF—, —C≡C—, —CH=CH—COO— or —OCO—CH=CH—, and n is an integer between 1 and 8.

The Z group is selected from:

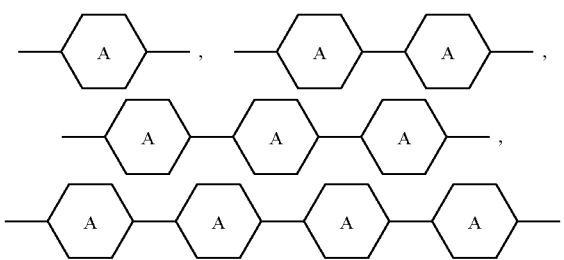

and any combination thereof, and the

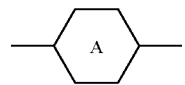

is a phenyl group, a substituted group thereof obtained by substituting one or more hydrogen atoms on the phenyl group with F, Cl, Br, I, —CN, —NO$_2$ or —C(=O)H, or a cycloalkyl group.

The R group is a straight or branched first alkyl group containing 5 to 20 carbon atoms, a first group obtained by substituting one —CH$_2$— group in the first alkyl group with phenyl, cycloalkyl, —CONN, —COO—, —O—CO—, —S—, —CO— or —CH—CH—, a second group obtained by substituting one of hydrogen atoms in the first alkyl group with an iron atom or a chlorine atom, or a third group obtained by substituting one of hydrogen atoms in the first group with an iron atom or a chlorine atom.

The L group is a polymerizable group attached to the Z group, the L group is at least one selected from:

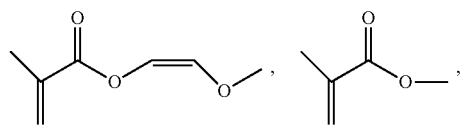

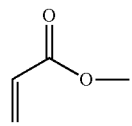

and any combination thereof.

According to a preferred embodiment of the disclosure, the auxiliary alignment agent comprises one A group, two Sp groups, one Z group, one R group, and one L group, and the structural formula of the auxiliary alignment agent is:

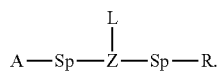

According to a preferred embodiment of the disclosure, the A group is selected from the group consisting of:

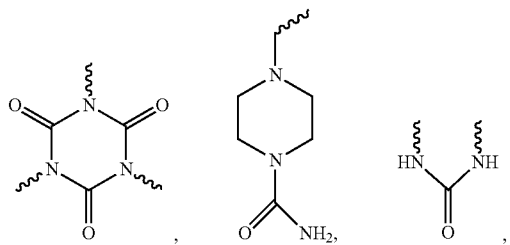

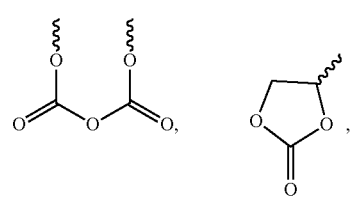

and any combination thereof.

According to a preferred embodiment of the disclosure, the structural formula of the auxiliary alignment agent is represented by one of formulas selected from:

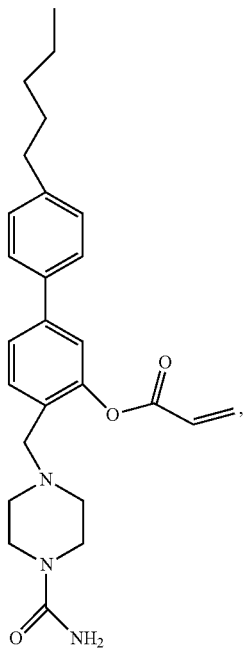

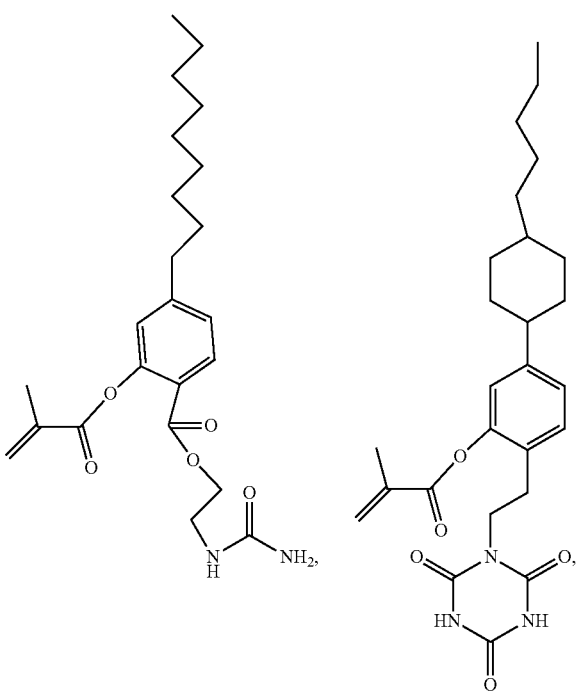

-continued

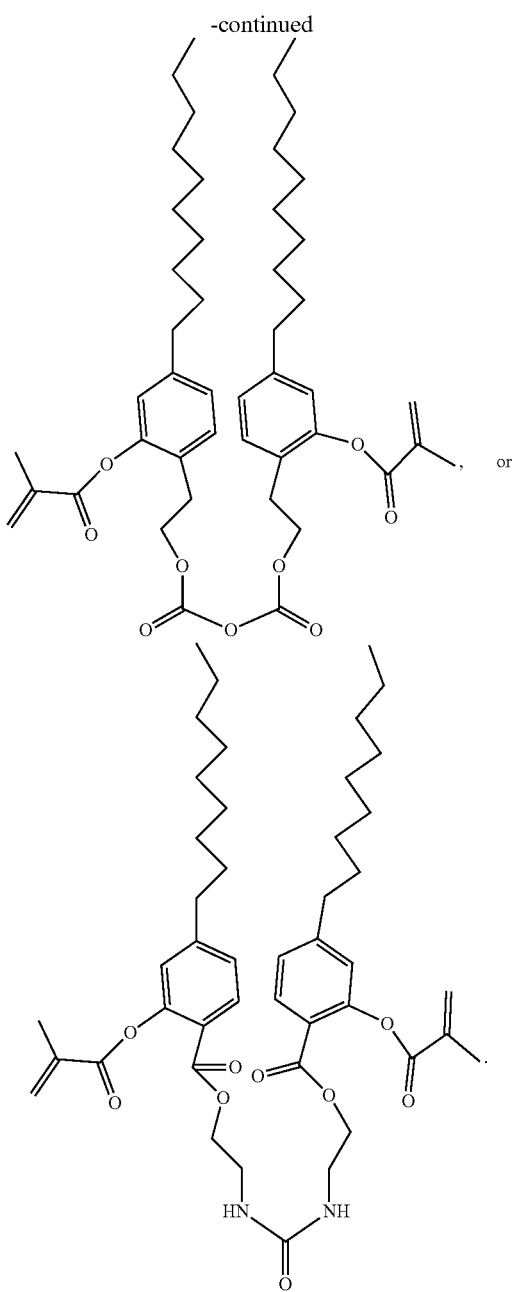

, or

According to a preferred embodiment of the disclosure, the polymerizable monomer includes one selected from the group consisting of an acrylate, an acrylate derivative, a methacrylate, a methacrylate derivative, styrene, a styrene derivative, an epoxy resin, and any combination thereof.

The disclosure further provides a liquid crystal display panel. The liquid crystal display panel comprises an array substrate, a color filter substrate disposed opposite to the array substrate, and a liquid crystal material disposed between the array substrate and the color filter substrate.

The liquid crystal material comprises liquid crystal molecules, a polymerizable monomer, and an auxiliary alignment agent.

A structural formula of the auxiliary alignment agent comprises at least one A group, at least one Sp group, at least one Z group, at least one R group, and at least one L group.

The A group comprises at least one oxygen atom, at least one nitrogen atom, or at least one oxygen atom and at least one nitrogen atom.

The Sp group is a —(CH$_2$)$_n$— group, or a substituted group thereof obtained by substituting one or more —CH$_2$ groups in the —(CH$_2$)$_n$— group with one or more groups selected from —O—, —S—, —CO—, —CO—O—, —O—CO—, —O—CO—O—, —OCH$_2$—, —CH$_2$O—, —CH=CH—, —CF=CF—, —C≡C—, —CH=CH—COO— or —OCO—CH=CH—, and n is an integer between 1 and 8.

The Z group is selected from:

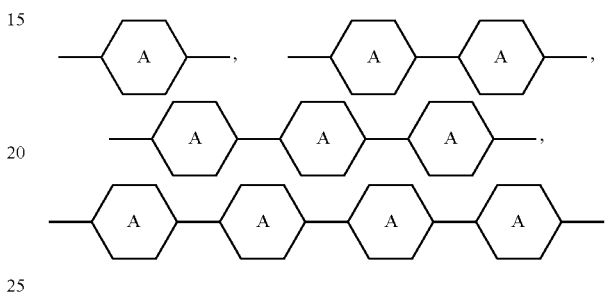

and any combination thereof, and the

is a phenyl group, a substituted group thereof obtained by substituting one or more hydrogen atoms on the phenyl group with F, Cl, Br, I, —CN, —NO$_2$ or —C(=O)H, or a cycloalkyl group.

The R group is a straight or branched first alkyl group containing 5 to 20 carbon atoms, a first group obtained by substituting one —CH$_2$— group in the first alkyl group with phenyl, cycloalkyl, —CONH, —COO—, —O—CO—, —S—, —CO— or —CH—CH—, a second group obtained by substituting one of hydrogen atoms in the first alkyl group with an iron atom or a chlorine atom, or a third group obtained by substituting one of hydrogen atoms in the first group with an iron atom or a chlorine atom.

The L group is a polymerizable group attached to the Z group, the L group is at least one selected from:

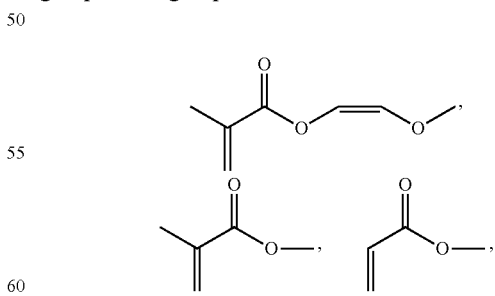

and any combination thereof.

According to a preferred embodiment of the disclosure, the auxiliary alignment agent comprises one A group, two Sp groups, one Z group, one R group, and one L group, and the structural formula of the auxiliary alignment agent is:

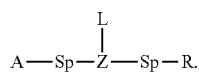
According to a preferred embodiment of the disclosure, the A group is selected from the group consisting of:
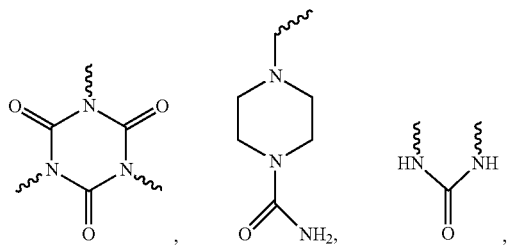
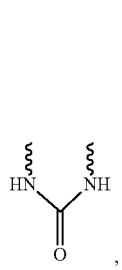
and any combination thereof.
According to a preferred embodiment of the disclosure, the structural formula of the auxiliary alignment agent is represented by one of formulas selected from:
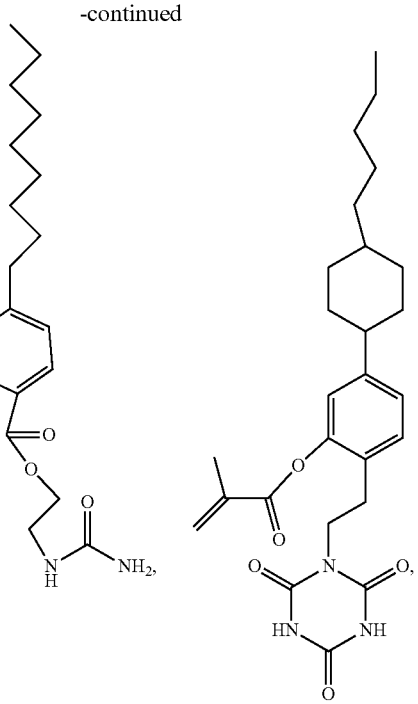
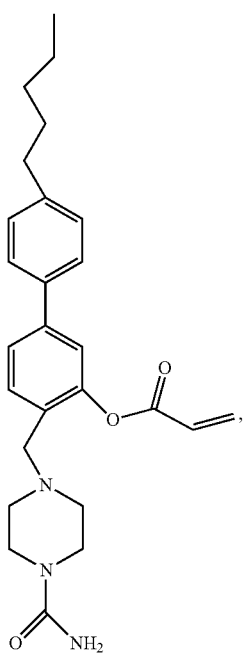
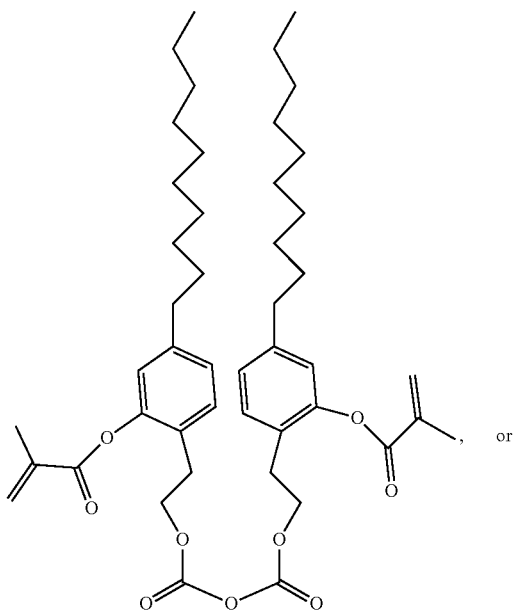

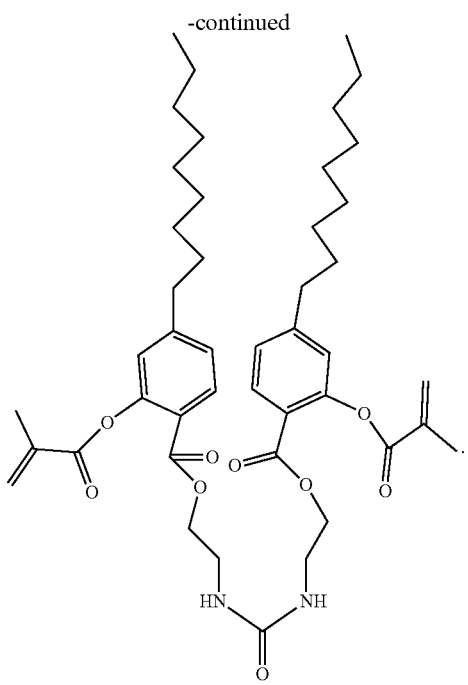

According to a preferred embodiment of the disclosure, the polymerizable monomer includes one selected from the group consisting of an acrylate, an acrylate derivative, a methacrylate, a methacrylate derivative, styrene, a styrene derivative, an epoxy resin, and any combination thereof.

The disclosure provides a liquid crystal material. The liquid crystal material comprises liquid crystal molecules, a polymerizable monomer, and an auxiliary alignment agent.

A structural formula of the auxiliary alignment agent comprises at least one A group, at least one Sp group, at least one Z group, at least one R group, and at least one L group.

The A group comprises at least one oxygen atom, at least one nitrogen atom, or at least one oxygen atom and at least one nitrogen atom.

The Sp group is a —(CH$_2$)$_n$— group, or a substituted group thereof obtained by substituting one or more —CH$_2$ groups in the —(CH$_2$)$_n$— group with one or more groups selected from —O—, —S—, —CO—, —CO—O—, —O—CO—, —O—CO—O—, —OCH$_2$—, —CH$_2$O—, —CH═CH—, —CF═CF—, —C≡C—, —CH═CH—COO— or —OCO—CH═CH—, and n is an integer between 1 and 8.

The Z group is selected from:

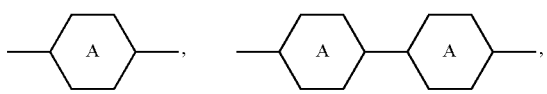

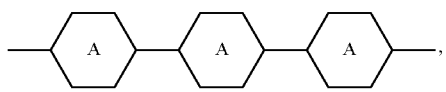

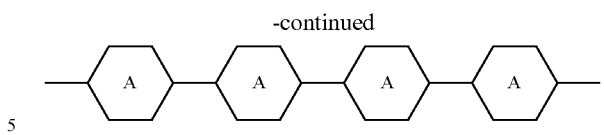

and any combination thereof, and the

is a phenyl group, a substituted group thereof obtained by substituting one or more hydrogen atoms on the phenyl group with F, Cl, Br, I, —CN, —NO$_2$ or —C(═O)H, or a cycloalkyl group.

The R group is a straight or branched first alkyl group containing 5 to 20 carbon atoms, a first group obtained by substituting one —CH$_2$— group in the first alkyl group with phenyl, cycloalkyl, —CONH, —COO—, —O—CO—, —S—, —CO— or —CH—CH—, a second group obtained by substituting one of hydrogen atoms in the first alkyl group with an iron atom or a chlorine atom, or a third group obtained by substituting one of hydrogen atoms in the first group with an iron atom or a chlorine atom.

The L group is a polymerizable group attached to the Z group, the L group is at least one selected from:

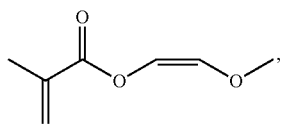

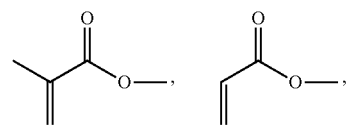

and any combination thereof.

According to a preferred embodiment of the disclosure, the auxiliary alignment agent comprises one A group, two Sp groups, one Z group, one R group, and one L group, and the structural formula of the auxiliary alignment agent is:

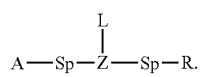

According to a preferred embodiment of the disclosure, the structural formula of the auxiliary alignment agent is represented by one of formulas selected from:

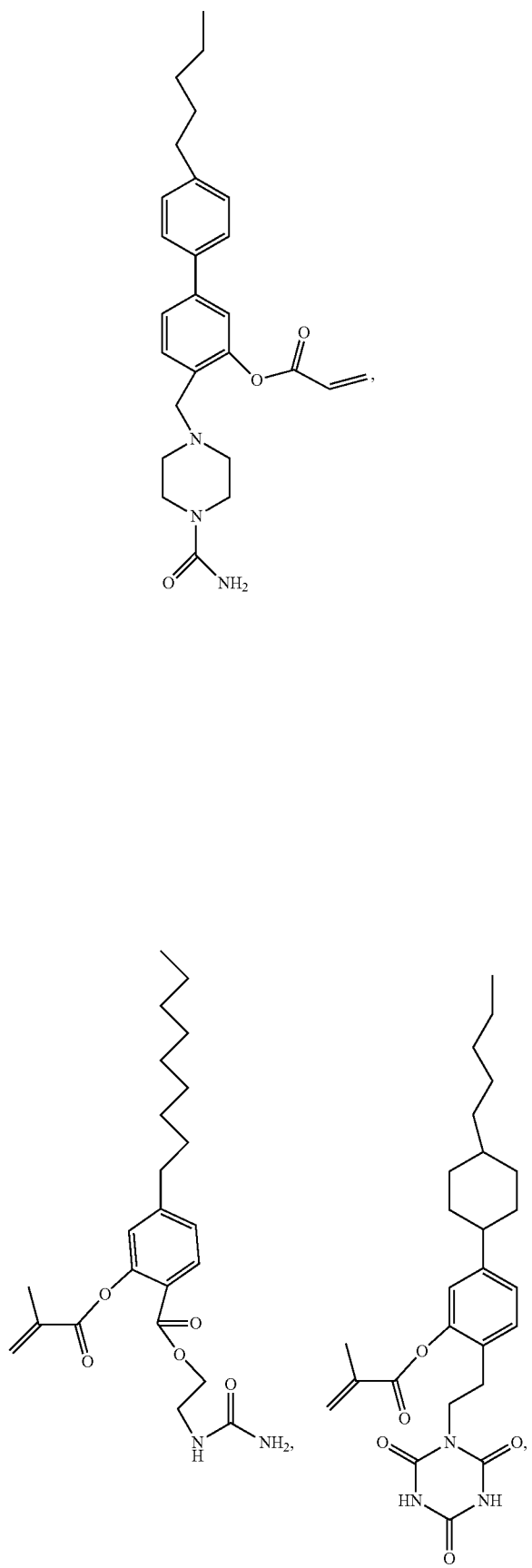

According to a preferred embodiment of the disclosure, the polymerizable monomer includes one selected from the group consisting of an acrylate, an acrylate derivative, a methacrylate, a methacrylate derivative, styrene, a styrene derivative, an epoxy resin, and any combination thereof.

The technical effects are as follows. Compared to conventional technologies, the disclosure provides the liquid crystal material and the liquid crystal display panel. The liquid crystal material comprises liquid crystal molecules, a polymerizable monomer, and an auxiliary alignment agent. A structural formula of the auxiliary alignment agent comprises at least one A group, at least one Sp group, at least one Z group, at least one R group, and at least one L group. The presence of the A group in the auxiliary alignment agent enhances the interaction of an additive material with SiNx/PFA, thereby solving the problems of alignment force difference, the drawbacks of the bright lines and the dark lines due to differences of the conventional pixel electrode. Therefore, the liquid crystal display panel can achieve the technical effect of uniform alignment. Moreover, the disclosure also eliminates PI materials and related PI processes and improves process efficiency.

DESCRIPTION OF DRAWINGS

In order to more clearly illustrate the embodiments of the present invention or the technical solutions in the prior art, the following briefly introduces the accompanying drawings used in the embodiments. Obviously, the drawings in the following description merely show some of the embodiments of the present invention. As regards one of ordinary skill in the art, other drawings can be obtained in accordance with these accompanying drawings without making creative efforts.

FIG. 1 is a flow chart of a manufacturing process of an auxiliary alignment agent in a liquid crystal material according to a preferred embodiment of this disclosure.

DETAILED DESCRIPTION OF PREFERRED EMBODIMENTS

This description of the exemplary embodiments is intended to be read in connection with the accompanying drawings, which are to be considered part of the entire written description. In the description, terms such as "lower", "upper", "horizontal", "vertical", "above", "below", "up", "down", "top", and "bottom", as well as derivatives thereof, should be construed to refer to the orientation as then described or as shown in the drawing under discussion. These terms are for convenience of description and do not require that the apparatus be constructed or operated in a particular orientation, and do not limit the scope of the disclosure. Referring to the drawings of the disclosure, similar components are labeled with the same number.

The disclosure provides a liquid crystal material. The liquid crystal material comprises liquid crystal molecules, a polymerizable monomer, and an auxiliary alignment agent.

The polymerizable monomer includes one selected from the group consisting of an acrylate, an acrylate derivative, a methacrylate, a methacrylate derivative, styrene, a styrene derivative, an epoxy resin, and any combination thereof.

A structural formula of the auxiliary alignment agent comprises at least one A group, at least one Sp group, at least one Z group, at least one R group, and at least one L group.

Preferably, in a preferred embodiment of the disclosure, the auxiliary alignment agent comprises one A group, two Sp groups, one Z group, one R group, and one L group, and the structural formula of the auxiliary alignment agent is:

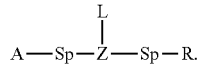

The A group comprises at least one oxygen atom, at least one nitrogen atom, or at least one oxygen atom and at least one nitrogen atom. In the disclosure, the A group is also referred to as "anchor group". The presence of the nitrogen atoms and oxygen atoms of the A group increases an interaction of an additive material with SiNx/PFA, so as to solve problems such as alignment force difference, and display defects of the bright lines and the dark lines due to differences of a pixel electrode. Preferably, the A group is selected from the group consisting of:

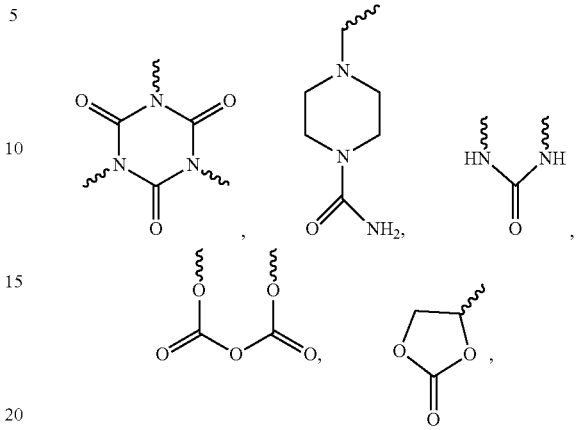

and any combination thereof.

In a preferred embodiment of the disclosure, the auxiliary alignment agent comprises two Sp groups located between the A group and the Z group, and between the Z group and the R group, respectively. The Sp group is a —(CH$_2$)$_n$— group, or a substituted group thereof obtained by substituting one or more —CH$_2$ groups in the —(CH$_2$)$_n$— group with one or more groups selected from —O—, —S—, —CO—, —OO—O—, —O—CO—, —O—CO—O—, —OCH$_2$—, —CH$_2$O—, —CH=CH—, —CF=CF—, —C≡C—, —CH=CH—COO— or —OCO—CH=CH—, and n is an integer between 1 and 8.

In a preferred embodiment of the disclosure, the auxiliary alignment agent comprises one of the Z groups, the Z group is located between two of the Sp groups. The Z group is selected from:

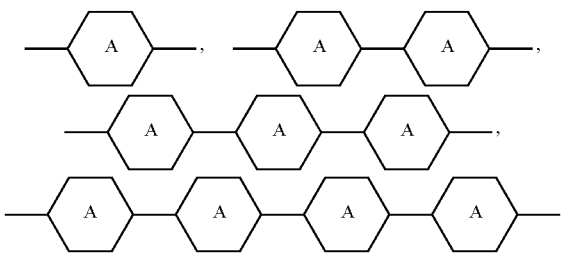

and any combination thereof.
Preferably, the

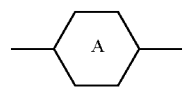

is a phenyl group, a substituted group thereof obtained by substituting one or more hydrogen atoms on the phenyl group with F, Cl, Br, I, —CN, —NO$_2$ or —C(=O)H, or a cycloalkyl group.

In a preferred embodiment of the disclosure, the auxiliary alignment agent comprises one of the R groups. The R group is linked to the Sp group. The R group is a straight or branched first alkyl group containing 5 to 20 carbon atoms, a first group obtained by substituting one —CH$_2$— group in the first alkyl group with phenyl, cycloalkyl, —CONH, —COO—, —O—CO—, —S—, —CO— or —CH—CH—, a second group obtained by substituting one of hydrogen atoms in the first alkyl group with an iron atom or a chlorine atom, or a third group obtained by substituting one of hydrogen atoms in the first group with an iron atom or a chlorine atom.

In a preferred embodiment of the disclosure, the auxiliary alignment agent comprises one of the L groups. The L group is a polymerizable group attached to the Z group. The L group is at least one selected from:

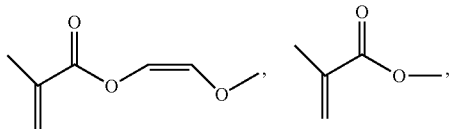

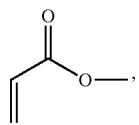

and any combination thereof.

Preferably, the structural formula of the auxiliary alignment agent is represented by one of formulas selected from:

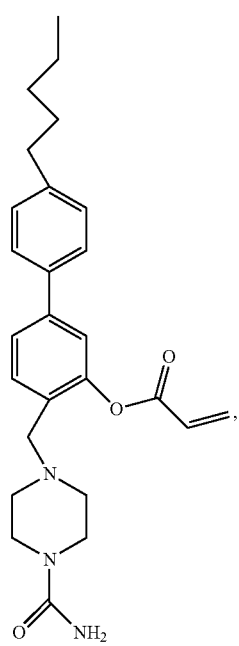

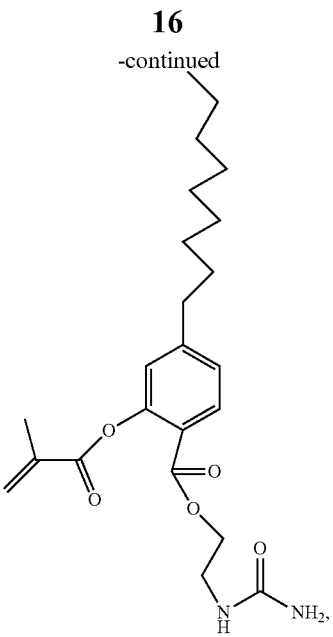

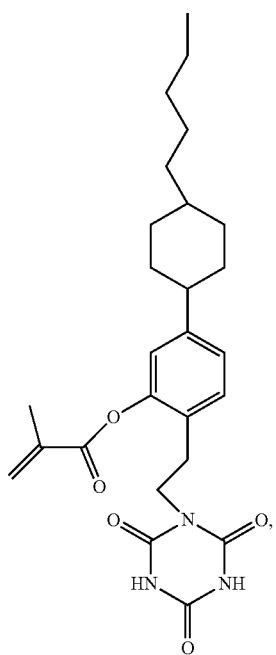

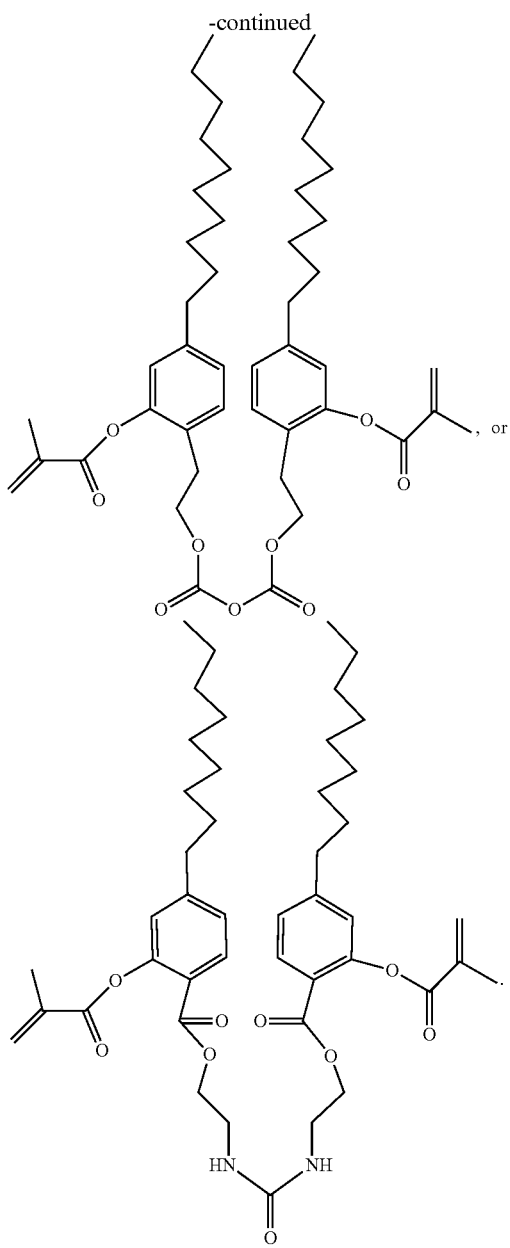

A following embodiment takes the auxiliary alignment agent (as shown below) as an example for describing a manufacturing process of the auxiliary alignment agent as shown in FIG. 1.

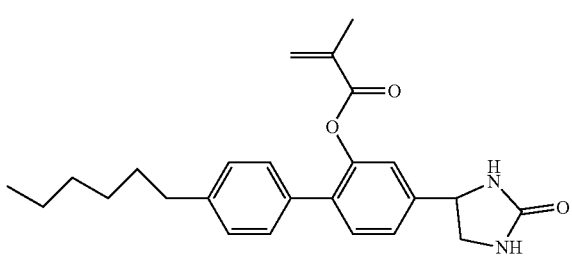

In a step S10, first of all, a substance a (0.02 mol) and a substance b (0.02 mol) of are dissolved in toluene (200 mL), and 100 mL of ethanol and 40 mL of $Na_2CO_3$ solution with a concentration of 1 mol/L are added into the toluene. A rare gas, such as argon, is introduced into the toluene. After 30 minutes, Tetrakis-(triphenylphosphine) palladium (100 mg) was added into the toluene so as to form a mixed solution. The mixed solution is heated to reflux for 60 min. Finally, after separation, a substance c is obtained.

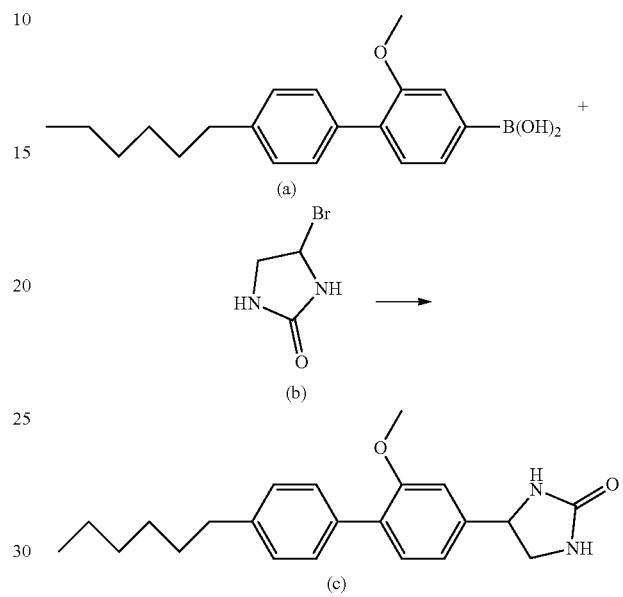

In a step S20, the compound c (0.01 mol) is dissolved in 50 mL of a dichloromethane solution and cool to −28° C. Then, 0.02 mol of boron trifluoride was added to the cooled mixed dichloromethane solution, and the cooled mixed dichloromethane solution is stirred at −25° C. for 3 hours while reacting. Finally, under a condition of an ice bath, a NaOH solution (having a substance concentration of 2 mol/L) is added to the mixed dichloromethane solution, and a substance d is obtained after separation and purification.

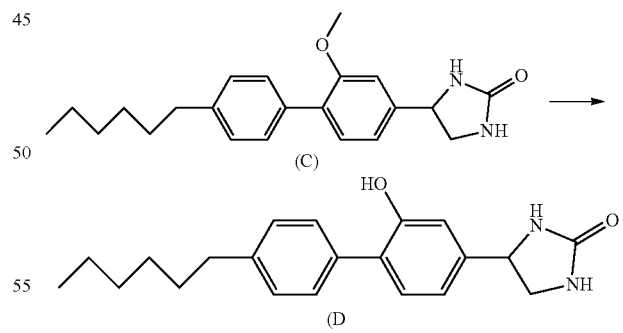

In a step S30, first of all, the compound d ($4×10^{-3}$ mol), methacrylic acid ($6×10^{-3}$ mol) and 4-(dimethylamino)pyridine ($2×10^{-4}$ mol) are dissolved in a dichloromethane solution (25 mL) for forming a mixed dichloromethane solution, and the mixed dichloromethane solution is cooled to 1° C. Secondly, the cooled mixed dichloromethane solution is gradually added dropwise a dichloromethane solution containing carbodiimide ($6×10^{-3}$ mol) so as to from a dropping process system. A temperature of the dropping process system is maintained at 1~4° C. Finally, a reaction of the dropping process system is stirred at a room temperature for 18 hours, and a compound e is obtained after separation and purification.

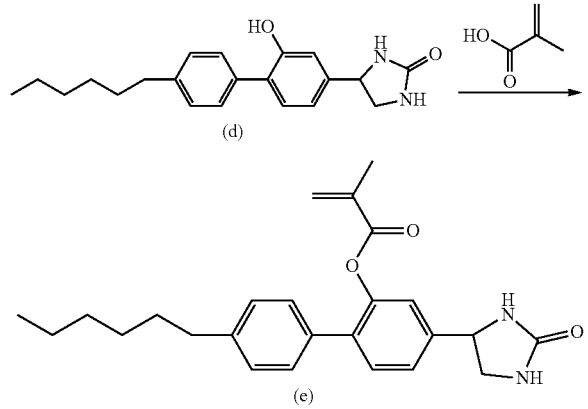

In this embodiment, H$^1$-NMR data for Compound e is as follows: δ: 0.96 (3H), 1.33 (2H), 1.29 (4H), 1.62 (2H), 2.55 (2H), 7.18 (2H), 7.43 (2H), 7.40 (1H), 6.99 (2H), 5.50 (1H), 3.71 (2H), 6.0 (2H), 5.49 (1H), 5.98 (1H), and 1.93 (1H).

The disclosure further provides a liquid crystal display panel. The liquid crystal display panel comprises an array substrate, a color filter substrate disposed opposite to the array substrate, and a liquid crystal material disposed between the array substrate and the color filter substrate.

The liquid crystal material comprises liquid crystal molecules, a polymerizable monomer, and an auxiliary alignment agent.

The polymerizable monomer includes one selected from the group consisting of an acrylate, an acrylate derivative, a methacrylate, a methacrylate derivative, styrene, a styrene derivative, an epoxy resin, and any combination thereof.

A structural formula of the auxiliary alignment agent comprises at least one A group, at least one Sp group, at least one Z group, at least one R group, and at least one L group.

Preferably, in a preferred embodiment of the disclosure, the auxiliary alignment agent comprises one A group, two Sp groups, one Z group, one R group, and one L group, and the structural formula of the auxiliary alignment agent is:

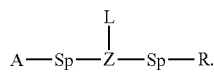

The A group comprises at least one oxygen atom, at least one nitrogen atom, or at least one oxygen atom and at least one nitrogen atom. In the disclosure, the A group is also referred to as "anchor group". The presence of the nitrogen atoms and oxygen atoms of the A group increases an interaction of an additive material with SiNx/PFA, so as to solve problems such as alignment force difference, and display defects of the bright lines and the dark lines due to differences of a pixel electrode. Preferably, the A group is selected from the group consisting of:

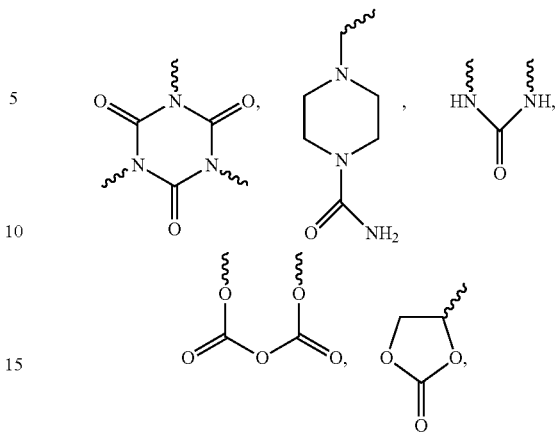

and any combination thereof.

In a preferred embodiment of the disclosure, the auxiliary alignment agent comprises two Sp groups located between the A group and the Z group, and between the Z group and the R group, respectively. The Sp group is a —(CH$_2$)$_n$— group, or a substituted group thereof obtained by substituting one or more —CH$_2$ groups in the —(CH$_2$)$_n$— group with one or more groups selected from —O—, —S—, —CO—, —OO—O—, —O—CO—, —O—CO—O—, —OCH$_2$—, —CH$_2$O—, —CH=CH—, —CF=CF—, —C≡C—, —CH=CH—COO— or —OCO—CH=CH—, and n is an integer between 1 and 8.

In a preferred embodiment of the disclosure, the auxiliary alignment agent comprises one of the Z groups, the Z group is located between two of the Sp groups. The Z group is selected from:

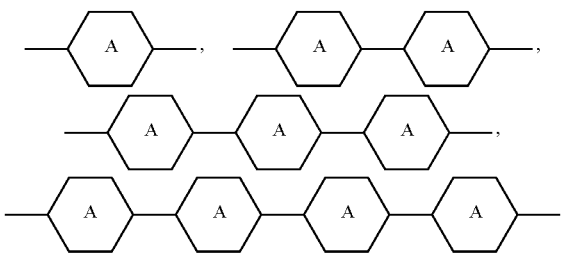

and any combination thereof.
Preferably, the

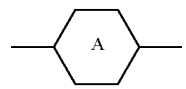

is a phenyl group, a substituted group thereof obtained by substituting one or more hydrogen atoms on the phenyl group with F, Cl, Br, I, —CN, —NO$_2$ or —C(=O)H, or a cycloalkyl group.

In a preferred embodiment of the disclosure, the auxiliary alignment agent comprises one of the R groups. The R group is linked to the Sp group. The R group is a straight or branched first alkyl group containing 5 to 20 carbon atoms, a first group obtained by substituting one —CH$_2$— group in the first alkyl group with phenyl, cycloalkyl, —CONN, —COO—, —O—CO—, —S—, —CO— or —CH—CH—, a second group obtained by substituting one of hydrogen atoms in the first alkyl group with an iron atom or a chlorine atom, or a third group obtained by substituting one of hydrogen atoms in the first group with an iron atom or a chlorine atom.

In a preferred embodiment of the disclosure, the auxiliary alignment agent comprises one of the L groups. The L group is a polymerizable group attached to the Z group. The L group is at least selected from:

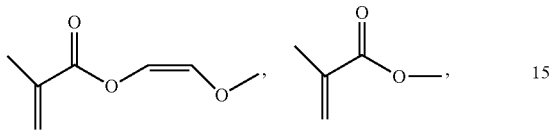

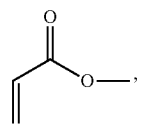

and any combination thereof.

Preferably, the structural formula of the auxiliary alignment agent is represented by one of formulas selected from:

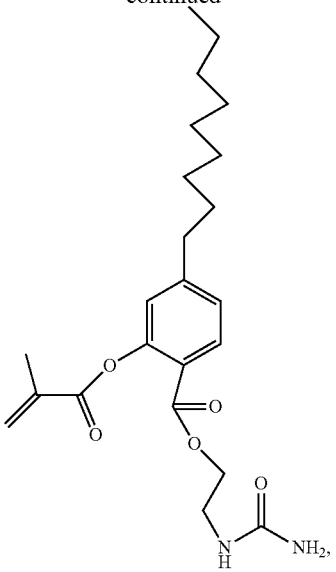

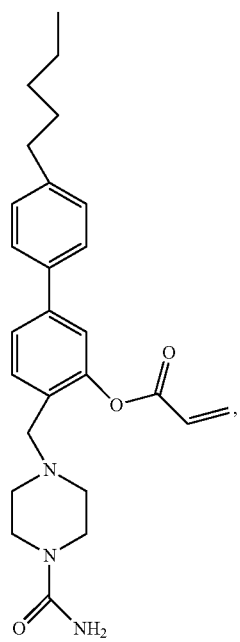

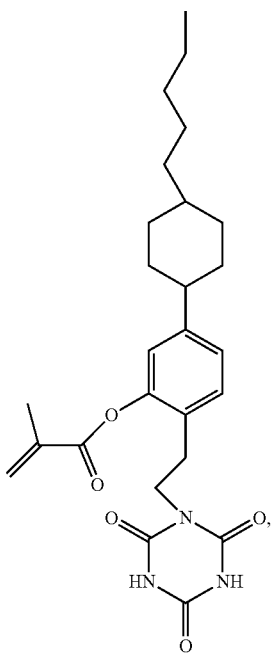

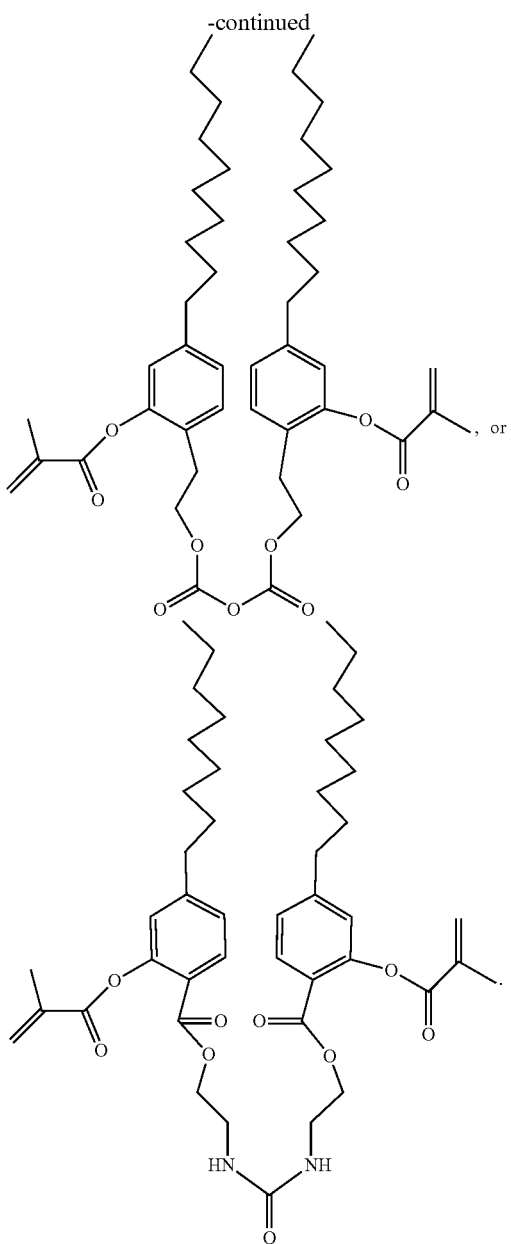
, or

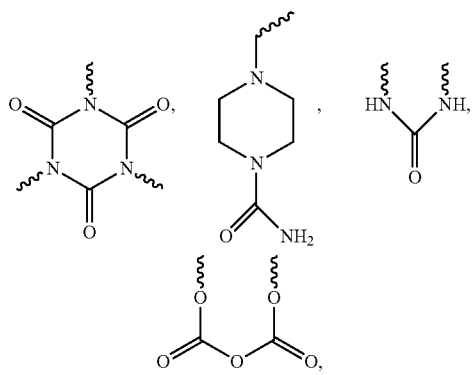

the disclosure provides the liquid crystal material and the liquid crystal display panel. The liquid crystal material comprises liquid crystal molecules, a polymerizable monomer, and an auxiliary alignment agent. A structural formula of the auxiliary alignment agent comprises at least one A group, at least one Sp group, at least one Z group, at least one R group, and at least one L group. The presence of the A group in the auxiliary alignment agent enhances the interaction of an additive material with SiNx/PFA, thereby solving the problems of alignment force difference, the drawbacks of the bright lines and the dark lines due to differences of the conventional pixel electrode. Therefore, the liquid crystal display panel can achieve the technical effect of uniform alignment. Moreover, the disclosure also eliminates PI materials and related PI processes and improves process efficiency.

This disclosure has been described with preferred embodiments thereof, and it is understood that many changes and modifications to the described embodiment can be carried out without departing from the scope and the spirit of the invention.

What is claimed is:

1. A liquid crystal material, comprising: liquid crystal molecules, a polymerizable monomer, and an auxiliary alignment agent;
wherein a structural formula of the auxiliary alignment agent is:

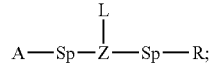

wherein the A group is selected from the group consisting of:

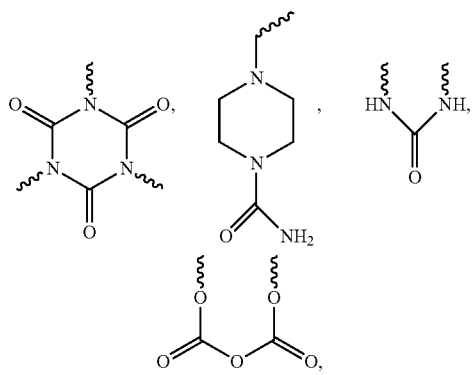

and any combination thereof;
wherein the Sp group is a —$(CH_2)_n$— group, or a substituted group thereof obtained by substituting one or more —$CH_2$ groups in the —$(CH_2)_n$— group with one or more groups selected from —O—, —S—, —CO—, —CO—O—, —O—CO—, —O—CO—O—, —OCH_2—, —CH_2O—, —CH=CH—, —CF=CF—, —C≡C—, —CH=CH—COO— or —OCO—CH=CH—, and n is an integer between 1 and 8;
wherein the Z group is selected from:

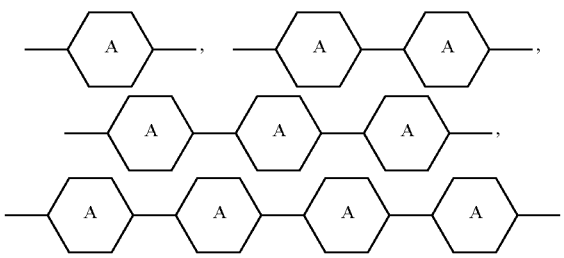

and any combination thereof, and the

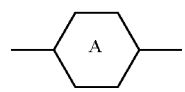

is a phenyl group, a substituted group thereof obtained by substituting one or more hydrogen atoms on the phenyl group with F, Cl, Br, I, —CN, —NO$_2$ or —C(=O)H, or a cycloalkyl group;

wherein the R group is a straight or branched first alkyl group containing 5 to 20 carbon atoms, a first group obtained by substituting one —CH$_2$— group in the first alkyl group with phenyl, cycloalkyl, —CONH, —COO—, —O—CO—, —S—, —CO— or —CH═CH—, a second group obtained by substituting one of hydrogen atoms in the first alkyl group with an iron atom or a chlorine atom, or a third group obtained by substituting one of hydrogen atoms in the first group with an iron atom or a chlorine atom; and wherein the L group is a polymerizable group attached to the Z group, the L group is at least one selected from:

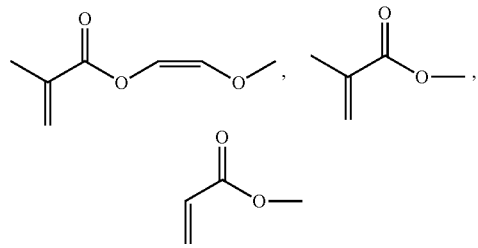

and any combination thereof.

2. A liquid crystal display panel, comprising: an array substrate, a color filter substrate disposed opposite to the array substrate, and a liquid crystal material disposed between the array substrate and the color filter substrate;

wherein the liquid crystal material comprises liquid crystal molecules, a polymerizable monomer, and an auxiliary alignment agent;

wherein the structural formula of the auxiliary alignment agent is represented by one of formulas selected from:

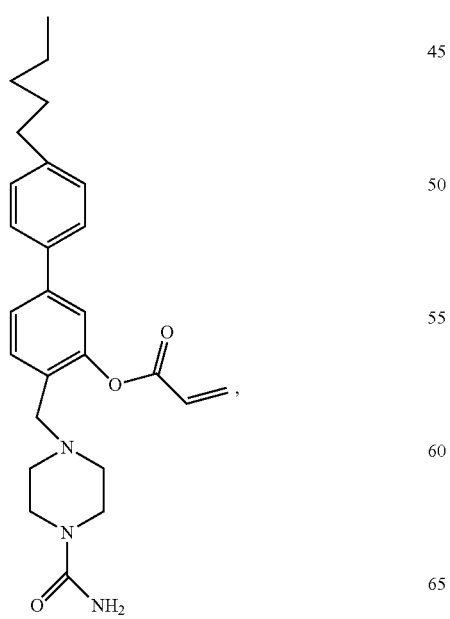

-continued

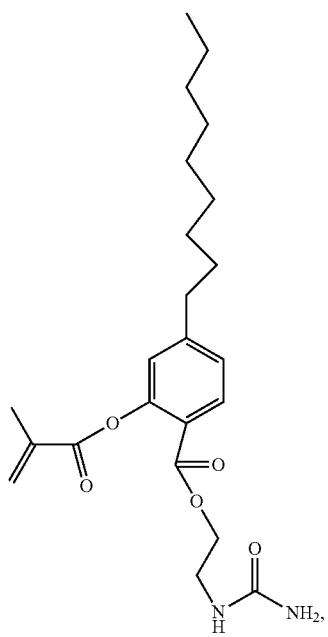

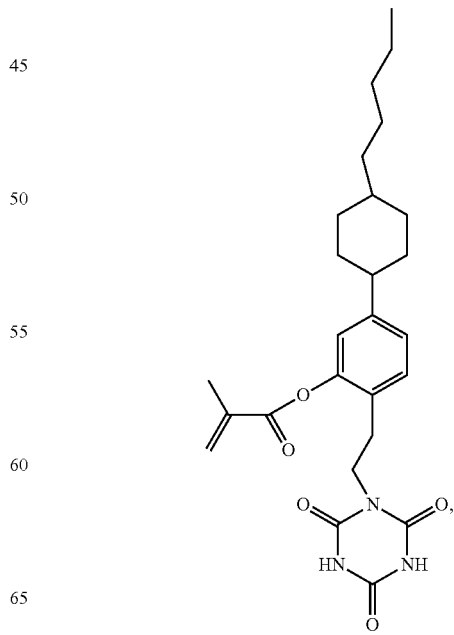

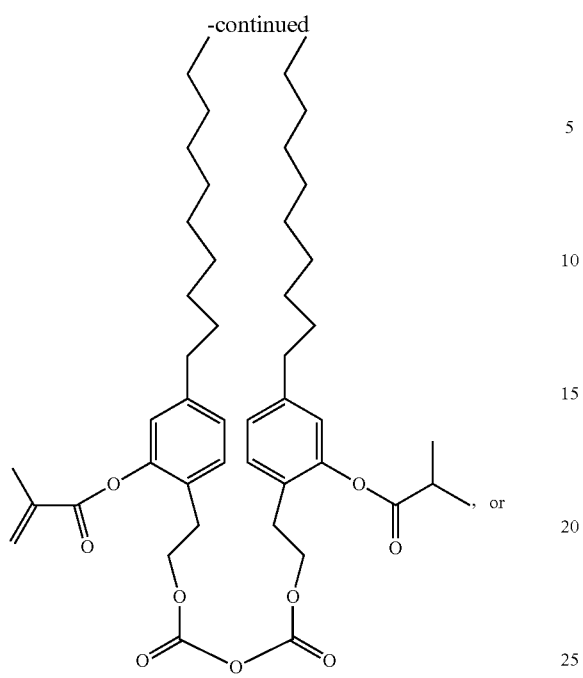

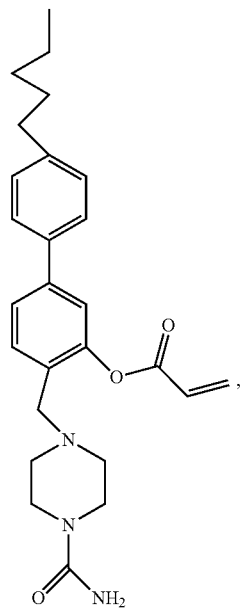

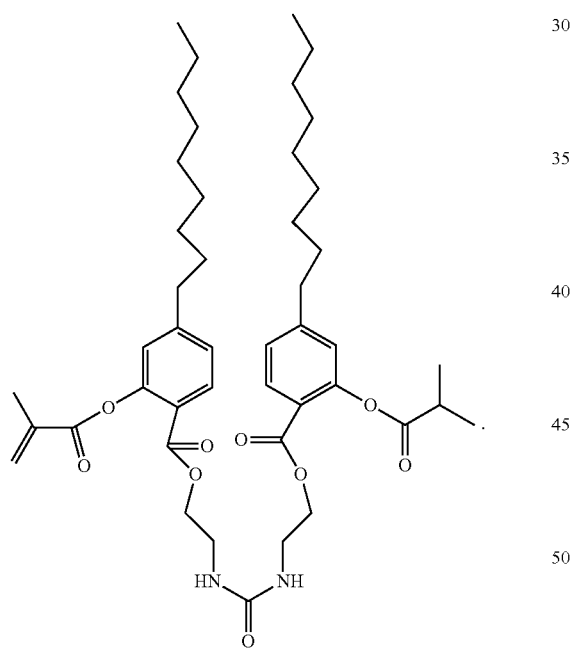

3. The liquid crystal display panel according to claim 2, wherein the polymerizable monomer includes one selected from the group consisting of an acrylate, an acrylate derivative, a methacrylate, a methacrylate derivative, styrene, a styrene derivative, an epoxy resin, and any combination thereof.

4. A liquid crystal material, comprising: liquid crystal molecules, a polymerizable monomer, and an auxiliary alignment agent;

wherein the structural formula of the auxiliary alignment agent is represented by one of formulas selected from:

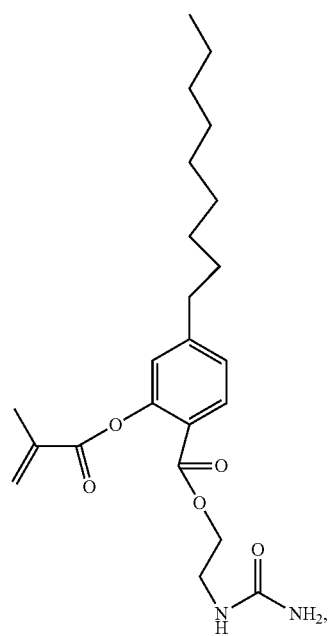

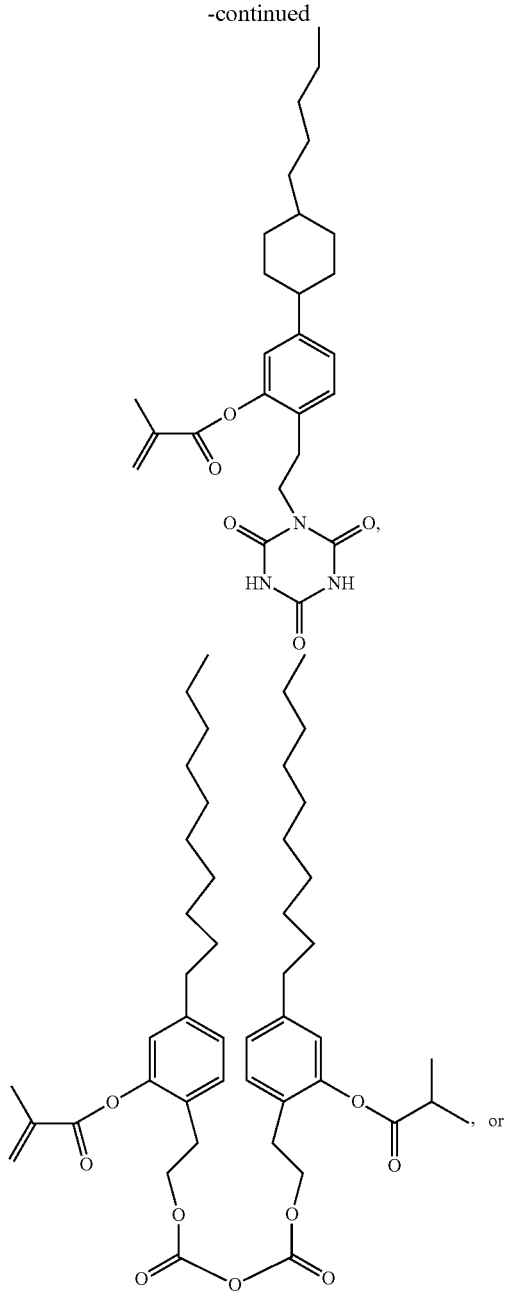
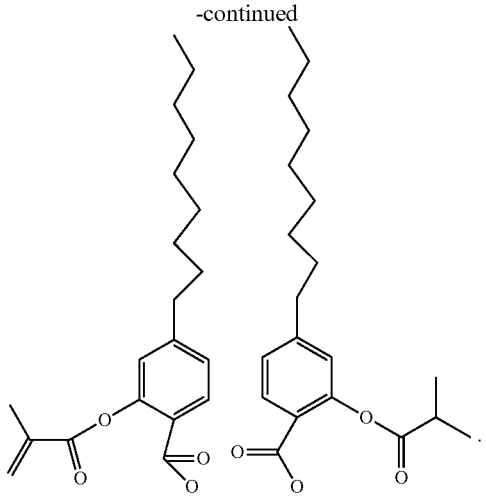
5. The liquid crystal material according to claim 4, wherein the polymerizable monomer includes one selected from the group consisting of an acrylate, an acrylate derivative, a methacrylate, a methacrylate derivative, styrene, a styrene derivative, an epoxy resin, and any combination thereof.
* * * * *